United States Patent
Brueggemann et al.

(10) Patent No.: US 6,329,324 B1
(45) Date of Patent: Dec. 11, 2001

(54) ACTIVE SUBSTANCE-CONTAINING COMPOSITION, ITS PRODUCTION AND ITS USE

(75) Inventors: Helmut Brueggemann; Erich Kuester, both of Krefeld (DE)

(73) Assignee: Stockhausen GmbH & Co. KG, Krefeld (DE)

(*) Notice: Subject to any disclaimer, the term of this patent is extended or adjusted under 35 U.S.C. 154(b) by 0 days.

(21) Appl. No.: 09/441,136

(22) Filed: Nov. 17, 1999

(30) Foreign Application Priority Data

Aug. 5, 1999 (DE) ............................................. 199 36 223

(51) Int. Cl.⁷ ................................................... A01N 25/04
(52) U.S. Cl. ............................................ 504/363; 514/938
(58) Field of Search .............................. 504/363; 514/938

(56) References Cited

U.S. PATENT DOCUMENTS

| | | | |
|---|---|---|---|
| 3,189,430 | 6/1965 | Kelly et al. | 71/2.6 |
| 3,479,176 | 11/1969 | Wilson | 71/94 |
| 4,123,249 | 10/1978 | Vartiak et al. | 71/66 |
| 4,786,681 | 11/1988 | Baker et al. | 524/710 |
| 5,599,768 | 2/1997 | Hermansky | 504/116 |

FOREIGN PATENT DOCUMENTS

| | | |
|---|---|---|
| 1023264 | 12/1977 | (CA) . |
| 30 04 248 | 8/1981 | (DE) . |
| 33 04 457 | 10/1983 | (DE) . |
| 36 28 091 | 2/1988 | (DE) . |
| 43 13 085 A1 | 10/1994 | (DE) . |
| 43 44 224 A1 | 6/1995 | (DE) . |
| 0 080 516 | 6/1983 | (EP) . |
| 0 201 214 | 11/1986 | (EP) . |
| 0 203 724 | 12/1986 | (EP) . |
| 0 272 374 A2 | 6/1988 | (EP) . |
| 420 497 A1 | 4/1991 | (EP) . |
| 0 481 226 | 4/1992 | (EP) . |
| 0 589 838 | 3/1994 | (EP) . |
| 0 734 206 | 10/1996 | (EP) . |
| 0 777 414 | 6/1997 | (EP) . |
| 0 887 004 | 12/1998 | (EP) . |
| 0 894 425 | 2/1999 | (EP) . |
| 1.544.172 | 9/1967 | (FR) . |
| WO 85/01736 | 4/1985 | (WO) . |
| WO 91/14365 | 10/1991 | (WO) . |
| WO 95/17455 | 6/1995 | (WO) . |
| WO 96/00251 | 1/1996 | (WO) . |
| WO 96/06526 | 3/1996 | (WO) . |
| WO 98/16103 | 4/1998 | (WO) . |

OTHER PUBLICATIONS

Database WPI, Section Ch, Week 198932, Derwent Abstracts, JP 01 165504, Jun. 29, 1989. XP–002154448.
Wolfgang Gerhartz, et al., Ullmann's Encyclopedia of Industrial Chemistry, vol. A11, pp. 251, 254, and 260, "Flocculants", 1988.

*Primary Examiner*—S. Mark Clardy
(74) *Attorney, Agent, or Firm*—Oblon, Spivak, McClelland, Maier & Neustadt, P.C.

(57) ABSTRACT

The invention relates to an active substance-containing composition comprising:

I. a water-in-oil polymer dispersion comprised of a continuous organic phase virtually immiscible with water, water-soluble and/or water-swellable polymer products finely dispersed therein, and optionally, auxiliary agents, and II. at least one active substance. The present invention also relates to the production of the active substance-containing composition and its use.

30 Claims, No Drawings

ACTIVE SUBSTANCE-CONTAINING COMPOSITION, ITS PRODUCTION AND ITS USE

The invention relates to an active substance-containing composition comprising:

I. a water-in-oil polymer dispersion comprised of a continuous organic phase virtually immiscible with water, water-soluble and/or water-swellable polymer products finely dispersed therein, and optionally, auxiliary agents, and II. at least one active substance.

The present invention also relates to the production of said active substance-containing composition and its use in placing active substances on or into substrates, preferably in agriculture, and particularly in plant and fruit cultivation, as well as in plant breeding, in storing or processing of fruits and field crops and plant materials such as wood.

After placing active substances such as pesticides on the surface of plants, seeds and wood, these substances are often washed off rapidly by water and consequently, have insufficient effect at the desired site of application and, in addition, frequently represent a hazard for the groundwater under such conditions.

Therefore, a number of attempts have been made to reduce said wash-off. To this end, oil-in-water dispersions have been used in the past, the action of which is based on the fact that aqueous solutions of active substances undergo more or less intense thickening, so that the wash-out process is reduced by the viscous state of these solutions.

The DE 36 28 091 A1 describes an aqueous polymer dispersion which, added with an active substance, is applied on a textile substrate. The polymer is coagulated on the fiber not before or after being coated thereon, so that the application is quite intricate. Once applied on the textile fabric, further contact of substrate and active substance with water is not intended. Thus, the formulation obviously is not used to prevent washing off of the active substance. Therefore, the use of the above-described formulation is inappropriate for e.g. agricultural purposes.

The EP 0,201,214 B1 discloses polymer products of essentially water-insoluble monomers, wherein the active substance is encapsulated. The objective of encapsulation is to have delayed release of active substance.

Aqueous dispersions are known from EP 0,589,838 A1, which contain a hydrophobic pesticide in the organic phase. Using this formulation, it is possible to distribute the water-insoluble active substance in an aqueous phase or provide a concentrate that can be diluted with water. Such an aqueous dilution may then be placed on e.g. agricultural lands.

Similar intentions as in the above-cited patent application are described in EP 0,080,516 A1. This written specification likewise teaches the incorporation of the active substance in an aqueous polymer dispersion of e.g. co-polymer products of styrene and acrylic acid.

Furthermore, the DE 33 04 457 A1 describes aqueous polymer dispersions in association with active substances, which are particularly suited for dusting in air.

WO 96/06526 describes a carrier for plant protection agents used to protect seed potatoes and based on paraffins, waxes, polydimethylsiloxanes and emulsifiers, as well as aqueous polymer dispersions which serve as adhesive solution. However, the production of the carrier is highly complex.

Similar products have been described for wood protection as well. The DE 30 042 48 A1 may be mentioned as an example, wherein an aqueous polymer dispersion is described as a formulating aid for wood protection agents, particularly aldrin.

The EP 0,203,724 B1 discloses the production of aqueous polymer dispersions which are remarkable for their special core-envelope particles, wherein polymer dispersions with water as continuous phase are described.

WO 96/00251 describes amphipathic graft copolymers of hydrophobic and hydrophilic monomers. Without exception, they are oil-in-water dispersions dilutable with water. Hydrophobic monomers are invariably used in the production of these formulating aids. For this reason, the thickening effect with viscosity increase of these formulations in an aqueous medium is not more than unsatisfactory.

While the above-cited written specifications are related to oil-in-water dispersions or emulsions, the following prior art is concerned with the use of water-in-oil dispersions, particularly in the agricultural field.

Thus, U.S. Pat. No. 4,123,249 describes a water-soluble polymer product in the form of a water-in-oil emulsion as formulating aid for algicides and herbicides, which thickens the solution of active substance during placing but lacks a polymer enclosing the active substance, so that the effect of this formulating aid against wash-out is unsatisfactory. The use of an inorganic crosslinker such as phytotoxic aluminum salts during placing the dispersion is described as optional. However, the use of phytotoxic crosslinkers substantially restricts the range of applications of this emulsion.

The patent specification CA 1,023,264 teaches the use of water-in-oil emulsions of such polymer products as additives in spray solutions for agricultural uses. In this process as well, the purpose of adding these emulsions is to increase the viscosity of the spray solution. This measure enables safe use of the spray or sprinkle solutions in the area of application even in windy conditions. The polymers present in the aqueous phase of the emulsion are not crosslinked.

Using these formulations, a prolonged period of action of the placed pesticides c an hardly be achieved.

The WO 91/14365 is concerned with the use of water-in-oil emulsions of water-soluble polymer products of polymers comprised of at least 50% of acrylamide in thickening solutions of a hydrophilic active substance to be sprayed, which is added to a polymer solution, so that the prolonged period of action described is inadequate as well.

Moreover, a sprayable, water-insoluble, film-forming active substance formulation for use on plants is known from EP 0,777,414 B1.

The EP 0,481,226 B1 teaches a powdered absorbent material releasing water and optionally nutrients and drugs to other bodies, preferably plants.

The EP 0,734,206 discloses storage-stable, liquid or dry, concentrated compositions containing glyphosate, one or more secondary alcohol surfactants and one or more other surfactants. Using th is composition, the effectiveness or rain resistance of pesticides and nutrients can be improved.

WO 85/01736 describes a hygroscopic coating composition for seeds, which consists of finely divided polyacrylamide and polyacrylate and an optional adhesion promoter. This composition is disadvantageous in that finely ground polyacrylamide and/or polyacrylate is difficult to handle, and the composition has poor adhesion on the seeds without an adhesion promoter.

Furthermore, the EP 0,887,004 describes a highly complex procedure for the protection of germinating seeds, wherein the seeds are coated with a gel and subsequently dried. The EP 0,894,425 describes an apparatus for coating seed grains with a gel.

It is therefore the object of the present invention to provide a liquid, active substance-containing formulation which is readily prepared and easy to apply, and where leaching problems of the active substance are cut back, which can be used as seed dressing, where optionally present toxicity to others than the target organisms and/or the environment is reduced, and where re-dosing of active substances or further, repeated applications are not required.

According to the invention, said object is accomplished by providing an active substance-containing composition which includes I. a water-in-oil polymer dispersion comprised of a continuous organic phase virtually immiscible with water, water-soluble and/or water-swellable polymer products finely dispersed therein, and optionally, auxiliary agents, and II. at least one active substance.

The active substance is preferably fixed on the polymer product, i.e., the active substance is adsorbed on the polymer product, incorporated in the polymer matrix, and/or enclosed by the polymer product upon contact of the composition of the invention with water or an aqueous solution.

Surprisingly, almost any active substance can be dispersed homogeneously in such a polymer dispersion, regardless whether it tends to be hydrophilic or hydrophobic in character. The polymer dispersion remains stable, even after addition of the active substance.

The composition according to the invention is also incorporated directly in the soil substrate. As a result, the active substances introduced in the soil substrate are retained for a longer period at the desired site, thereby significantly increasing the activity and the period of action of the active substance.

In the meaning of the invention, a water-in-oil polymer dispersion comprises both a polymer emulsion and a polymer suspension as described in e.g. Ullmann's Encyclopedia of Industrial Chemistry, 1988, Vol. A11, page 254, which hereby is incorporated by reference and thus, is understood to be part of the disclosure.

The inverse polymer product dispersions contained in the composition according to the invention are a class of products preferably prepared by water-in-oil polymerization. To this end, finely dispersed water-soluble and/or water-swellable polymer products are generated in a continuous organic phase virtually immiscible with water, with addition of water-in-oil emulsifiers and/or dispersants and optionally wetting agents.

Aromatic and aliphatic linear, branched and cyclic hydrocarbons are preferably used as hydrophobic organic liquids, including hydrocarbons or mixtures thereof, preferably n- and/or isoparaffins, and particularly distillation products of predominantly paraffinic and naphthene-base petroleum. In addition, linear and branched liquid esters of natural and synthetic origin may also be used. These include natural oils, the main components of which predominantly being triglycerides having a carboxylic acid portion derived from ethylenically mono- or polyunsaturated and saturated $C_{10}$–$C_{30}$ fatty acids, as well as esters with aliphatic alcohols produced therefrom. The above-mentioned substances are also employed as hydrophobic, organic phase in any combination or various combinations of each other with respect to composition and quantity.

The monomer-containing water-in-oil dispersion is produced in order to prepare the polymerization, wherein oil-soluble emulsifiers having a low HLB value, such as partial esters of glycerol, di- and polyglycerol, sorbitol, sorbitan, and addition products of alkylene oxides such as ethylene oxide and propylene oxide with higher linear and branched alcohols or alkylphenols are employed. It is also preferred to use so-called polymeric emulsifiers alone or in admixture as described in, inter alia, U.S. Pat. No. 4,786,681 which hereby is incorporated by reference and thus, is understood to be part of the disclosure.

The polymer products are produced in such a way that at least one water-soluble, monoethylenically unsaturated monomer, alone or together with polyreactive, preferably ethylenically polyunsaturated monomers acting as crosslinkers, is polymerized in the aqueous phase of a water-in-oil polymer dispersion in the presence of dispersants and/or preferably emulsifiers and optionally wetting agents and conventional polymerization initiators having a free-radical effect. The water-soluble, monoethylenically unsaturated monomers may optionally be copolymerized together with water-insoluble, monoethylenically unsaturated monomers such as vinyl acetate where, as a common rule, the water-insoluble monomers are employed in only such an amount that water-soluble or water-swellable polymer products are still formed. Such polymer products and the production of polymer products according to the inverse process of water-in-oil polymerization are well-known.

Exemplary water-soluble, monoethylenically unsaturated compounds are monoethylenically unsaturated carboxylic acids such as acrylic acid, methacrylic acid, maleic acid, itaconic acid, salts of these carboxylic acids, e.g. sodium, potassium or ammonium salts, acrylic acid and (meth) acrylic acid esters of aminoalcohols, such as dimethylaminoethyl acrylate in protonated or quaternized form, e.g. dimethyl-aminoethyl acrylate hydrochloride, dimethylaminoethyl acrylate hydrosulfate, trimethylammoniumethyl acrylate chloride, trimethylammoniumethyl acrylate methosulfate, dimethylaminoethyl methacrylate hydrochloride, dimethylaminoethyl methacrylate hydrosulfate, trimethylammoniumethyl methacrylate chloride, dimethylethylammoniumethyl methacrylate ethosulfate, acrylamide, methacrylamide, N-alkylated (meth)acrylamides, dialkylaminoalkylacrylamide, and dialkylaminoalkyl methacrylamides, and the acid salts and quaternized forms of the ammonium salts, such as methacrylamidopropyltrimethylammonium chloride, acrylamidopropyltrimethylammonium chloride, methacrylamidopropyltrimethylammonium methylsulfate, acrylamidopropyltrimethylammonium methylsulfate, and also, acrylamido- and methacrylamidoalkylsulfonic acids, such as 2-acrylamido-2-methylpropanesulfonic acid, and their salts, e.g. Na, K or ammonium salts, hydroxyalkyl acrylates and hydroxyalkyl methacrylates, vinylsulfonic acid, vinylphosphonic acid, N-vinylamides, such as N-vinylformamide, N-vinylacetamide, N-vinyl-N-methylacetamide, and N-vinyl-N-methylformamide, diallyldimethylammonium chloride, N-vinylpyrrolidone, N-vinylimidazole, N-vinylimidazoline, 2-methyl-1-vinylimidazoline, 2-sulfoethyl methacrylate, styrenephosphonic acid, and styrenesulfonic acid.

In addition, suitable water-soluble monomers are N-methylolacrylamide, N-methylolmethacrylamide, as well as N-methylol(meth)acrylamides partially or completely etherified with monohydric $C_1$–$C_4$ alcohols. The water-soluble monomers can be polymerized either alone or in mixtures of each other to form water-soluble polymer products. They are copolymerized at any desired ratio.

Water-swellable polymer products are obtained by polymerizing at least one water-soluble, monoethylenically unsaturated monomer together with at least one crosslinker. The amounts of crosslinker employed depend on the type of crosslinker and range from 0.001 up to 10 wt.-%, relative to the amount of monomers employed. The amount of crosslinker preferably is from 0.01 to 1 wt.-%. For example, the cross-linkers contain at least two non-conjugated, ethylenically unsaturated double bonds. Suitable crosslinkers are e.g. N,N'-methylenebisacrylamide, ethylene glycol diacrylate and -methacrylate, polyethyleneglycol diacrylate and -dimethacrylate, propylene glycol diacrylate, butanediol diacrylate, hexanediol diacrylate and -dimethacrylate, diacrylates and dimethacrylates of block copolymers of alkylene oxides such as ethylene oxide and propylene oxide, addition products of ethylene oxide and/or propylene oxide with glycerol, pentaerythritol or trimethylolpropane di- or triesterified with acrylic acid or methacrylic acid, polyhydric alcohols such as glycerol or pentaerythritol or trimethylolpropane at least diesterified with acrylic acid or methacrylic acid, polyhydric alcohols such as glycerol or pentaerythritol or trimethylolpropane at least dietherified with allyl groups or their addition products with ethylene oxide and/or propylene oxide; triallylamine, tetraallylethylenediamine, divinylbenzene, diallyl phthalate, polyethyleneglycol divinyl ether, butanediol divinyl ether, divinylethylene urea, triallylamine or its quaternized derivatives, e.g. triallylmethylammonium chloride and tetraallylammonium chloride. It is preferred to use water-soluble crosslinkers, e.g. N,N'-methylenebisacrylamide, polyethyleneglycol diacrylates or dimethacrylates and/or triallylmethylammonium chloride.

By varying the water/oil ratio, the viscosity of such compositions can be varied in a wide range and thus, adapted to the intended use.

For example, the actual composition according to the invention is used as spray fluid, being applied on substrates or mixed with materials. The active substance preferably is spread uniformly on any desired surface such as peat, mulch, rock wool, swelled aqueous gels, preferably of superabsorbers, natural and/or synthetic fiber blends, fabrics, fleeces or wadding, on plant parts like trunks, branches, blossoms and leaves, whole or divided roots or tubers, as well as on surfaces of seed grains and seeds, and optionally incorporated.

The composition of the invention is suitable for use against most various organisms harmful for plants or plant parts, such as bacteria, viruses, mites, aphids, insects, insect larvae, snails, nematodes, rodents, or in the prevention thereof.

Accordingly, the composition of the invention contains biologically active substances as active ingredients, and preferably, the following substances as biocidal active substances: acaricides, algicides, aphicides, bactericides, fungicides, herbicides, insecticides, larvicides, molluskicides, nematicides, rodenticides, viricides. However, active substances such as inhibitors for plants, e.g. against algae, fungi, grasses, and so-called weed plants, as well as growth promoting substances such as fertilizers and plant growth promoters, plant growth regulators, repellents, as well as agents capable of enhancing the resistance of plants to harmful organisms or substances are preferred.

As to the type of active substances, there is no restriction amongst the compositions of the invention, in principle. The group of insecticides may be exemplified as follows: organophosphates, pyrethroids, pyrethrum, carbamates, chlorinated hydrocarbons, benzoylurea derivatives, as well as substances obtained by means of biosyntheses, such as BT types, BS and similar, related types. The group of herbicides may be exemplified as follows: triazines, amides, carbamates, urea derivatives, diazines, diphenyl ethers, sulfonylureas, and imidazole derivatives. The group of fungicides may be exemplified as follows: benzimidazoles, triazoles, organophosphates, morpholines, and dithiocarbamates.

In addition to the above-mentioned compounds, odorous substances are also possible as active substances. In this respect, pheromones are of particular importance. With chemical compatibility of the components, common pheromones and other odorous substances may also be ingredients of the composition according to the invention.

Both phases of the water-in-oil polymer dispersion are suitable as carriers or solvents for an active substance. In general, one could say that hydrophilic active substances are entirely or predominantly contained in the aqueous polymer phase of the water-in-oil polymer dispersion, whereas hydrophobic substances are entirely or predominantly contained in the oil phase of the water-in-oil polymer dispersion.

Also, hydrophobic active substances such as isopropyl (E,E)-11-methoxy-3,7,11-trimethyl-2,4-dodecanedienoate (Methoprene®) may partially or completely replace the oil phase. In this event, the oil phase of the water-in-oil polymer dispersion and the active substance are identical.

Fundamentally, hydrophilic and predominantly hydrophilic, as well as hydrophobic and predominantly hydrophobic substances are suitable as active substances in the composition of the invention. In some cases, however, the type of emulsifier, polymer and/or the nature of the oil phase have to be adapted to the active substance to be formulated.

The composition of the invention may include multiple active substances, and the respective active substance may be located in one or in both phases of the water-in-oil polymer dispersion.

The active substances may also form adducts with the polymer or another ingredient of the polymer dispersion. Such an effect is desirable as long as adduct formation does not proceed in an irreversible fashion.

As described above, hydrophobic active substances may constitute the oil phase of the polymer dispersion. Accordingly, the quantity ratio of the hydrophobic active substances can be a maximum-of 100 wt.-% of the oil phase. However, those active substance-containing compositions are preferred wherein the ratio of active substance is 50 wt.-% at maximum, more preferably 25 wt.-% of the oil phase at maximum.

Hydrophilic active substances preferably dissolve in the water phase or become incorporated therein. The hydrophilic active substance ratio can be 60 wt.-% at maximum, preferably 40 wt.-% at maximum, and more preferably 25 wt.-% of the aqueous phase at maximum.

The viscosity of the polymer dispersion can be adjusted variably over a wide range and thus, adapted to the respective purpose.

The formulation according to the invention is produced according to 3 possible procedures:

1) The active substance is added to the monomer solution or the oil phase prior to polymerization, where the oil phase itself can be the active substance. A precondition for this method is that the active substance will not undergo undesirable reactions during polymerization, e.g. with termination of the polymerization.
2) The active substance, optionally together with additional agents, is introduced as total amount or as partial amount or with continuous metering during polymerization. Likewise, a precondition is that the active substance will not react in an undesirable fashion.
3) The active substance is added to the polymer dispersion subsequent to polymerizing. Particularly in case of hydrophilic active substances or when adding aqueous solutions or dispersions of active substances, thorough mixing of the components is provided because otherwise, partial excess concentrations would give rise to breaking of the polymer dispersion and to subsequent gelling thereof.

The production of the active substance formulation is effected at temperatures ranging between 0 and 110° C., preferably between 20 and 80° C.

The compositions of the invention are used in all those fields where active substances suffer losses of their effectiveness due to biotic and abiotic environmental factors. In particular, they are used where losses have been occurring so far as a result of climatic factors, such as heat, cold, light, wind, moisture or precipitation, as well as chemical factors, e.g. impairment of the active substance by oxygen, carbon dioxide, trace gases, and plant nutrients, as well as mechanical factors, such as undesirable distribution of the active substance by air and water currents, such as wind and wave motions, or uncontrolled sedimentation. Moreover, losses as a result of orographic factors, such as unfavorable distribution due to surface structures of the substrates, materials and surfaces to be treated, and their location, e.g., inclination of hillsides in the terrain, or other delocalization of the active substance, and undesirable distribution of the active substance as a result of edaphic factors, the physical and chemical nature of the soil, will be eliminated or at least reduced when using the active substance-containing composition according to the invention.

The active substance-containing compositions of the invention are easy to handle and stable when stored, stability being particularly important with respect to the effectiveness of the active substance. The compositions are handled directly as such, or initially as an active substance concentrate, and subsequently used in a dilute form.

Dilution may be effected by adding hydrophobic liquids which are also suitable as hydrophobic phase of the polymer dispersion, e.g. liquid aliphatic n- and or isoparaffinic hydrocarbons summarized under the generic term of white oils.

Dilution may also be effected in such a way that the composition of the invention is added to, dissolved, partially dissolved, or dispersed in water.

The advantages of such formulations are, e.g. improved storage stability, increased viscosity of the solution to be used, and a stabilization of the active substance subsequent to placing on or into a substrate. Furthermore, substances of intensive odor are incorporated in the concentrate in such a way that malodor caused by the active substance is substantially reduced.

Typical concentrations to be used range from 0.1 to 10.0 wt.-%, preferably from 0.5 to 5 wt.-% of the composition, relative to the respective composition or the respective active substance used.

In addition, the compositions of the invention may also be incorporated in the aqueous medium in a concentrated form, a compact gel being formed after phase inversion. The active substance then is released from the compact gel mass over a prolonged period of time.

If the compositions are used in accordance with the invention, the active substance will be gradually released from the gel particles upon admission of water, where controlled release of the active substance into the environment with respect to time and quantity (controlled release effect), i.e., a delayed or accelerated release of active substance is achieved, which is biased or controlled by the materials making up the composition.

The compositions of the invention and the dilutions produced therefrom are applied on or into substrates, preferably by spreading, immersing or spraying, or mixed with the substrate to be treated.

When applying the compositions according to the invention on plants, e.g. in the treatment of vines on hillside areas, premature wash-off of the active substances—the so-called run-off effect—is significantly reduced, i.e., the active substance applied with the composition of the invention will not be washed off so quickly by falling rain and will reach the nearby running waters to a significantly reduced extent.

Similarly, when using the compositions according to the invention in soil or soil substrates, the active substance is stored in a stable fashion and has improved availability in the upper soil layers because the active substance after rainfalls will not be leached from the soil either, or to a significantly reduced extent, so that the so-called leaching effect where the active substance is conveyed into deeper soil layers and into the ground water is reduced or does not occur at all.

Additional preferred uses of the active substance-containing composition according to the invention are:

The use of the active substance-containing composition as seed dressing. Surprisingly, the compositions are particularly suited for this special use which, e.g. with fungicides as active substance, permits favorable and adherent distribution of the active substance bound in the finely divided polymer product over the individual seed grains. Upon admission of moisture or water, formation of the active substance-containing aqueous gel on the seed grains proceeds spontaneously. The use of the active substance-containing composition in insect control. To this end, the composition is placed in hotbeds of insects where it is stored as a stable preparation until spontaneous formation of the gel is effected by admission of moisture or water, from which gel the active substance, e.g. an insecticidal and/or larvicidal formulation, is released in a controlled fashion. Preferably, hotbeds of mosquitos are treated in this way. Special uses involve the application of the compositions of the invention in condensation water tanks of air conditioners and on tires, particularly on used tires, by spraying or spreading the dispersion.

In these cases, the insecticide will take effect upon admission of water in the form of condensation or rain water.

Without intending to be limiting, some examples of the active substance-containing composition of the invention will be given hereinbelow which are to demonstrate the idea of the invention.

The following abbreviations will be used herein:

| ABAH | Azobisamidinopropane dihydrochloride |
| AMPS | 2-Acrylamido-2-methylpropanesulfonic acid |
| TAMAC | Triallylmethylammonium chloride |

EXAMPLE 1

In this example, the active substance is added to the final water-in-oil polymer dispersion.

To prepare the polymer dispersion, an aqueou s monomer solution is initially produced from the following components:

430 g of water
88 g of AMPS, sodium salt, 50% solution
227 g of acrylamide, 50% solution
332 g of acrylic acid
332 g of sodium hydroxide solution, 50%
0.6 ml of thioglycolic acid
1.0 ml of Versenex® 80
5.0 ml of TAMAC 0.6 g of ABAH There after, 40 g of Arlacel® 987 is dissolved in 480 g of Shellsol® D 100, and the aqueous monomer solution is added with stirring. After formation of the water-in-oil polymer dispersion, it is homogenized with a fast running household mixer, and the water-in-oil polymer dispersion is made free of dissolved oxygen by purging with nitrogen. The polymerization is catalyzed at 20° C. with 2 ml of a 0.2% tertbutyl hydroperoxide solution and 2.4 ml of sulfur dioxide gas, and the batch is heated up to about 100° C. by the generated heat of polymerization. Following cooling, 40 g of 6-nonylphenol ethoxylate and 20 g of 9-nonylphenol ethoxylate are added with stirring.

The polymer product is comprised of 25 mole-% acrylamide, 72 mole-% of a partially neutralized acrylic acid, and 3 mole-% AMPS.

The final water-in-oil polymer dispersion is added once with 2% Bronopol®, which is a bacteriostatic agent (2-bromo-2-nitropropane-1,3-diol), and once with 5% Bronopol®, and stirring is effected for 2 to 5 hours each time, until the crystals have completely dissolved. Depending on the concentration, more or less viscous solutions are obtained when adding the active substance-containing composition to water.

EXAMPLE 2

In this example, the active substance Methoprene® (=isopropyl (E,E)11-methoxy-3,7,11-trimethyl-2,4-dodecane-dienoate) is added as early as prior to the actual polymerization.

To prepare the polymer dispersion, an aqueous monomer solution is initially produced from the following components:
490 g of water
234 g of acrylamide, 50% solution
358 g of acrylic acid
358 g of sodium hydroxide solution, 50%
0.6 ml of thioglycolic acid
1.0 ml of Versenex® 80
5.0 ml of TAMAC
0.3 g of ABAH
0.4 g of VA-044

Thereafter, 30 g of Hypermer® 2296 is dissolved in 416 g of Shellsol® D 100 and 100 g of Methoprene®, and the aqueous monomer solution is added with stirring. After formation of the water-in-oil polymer dispersion, it is homogenized with a fast running household mixer, and the polymer dispersion is made free of dissolved oxygen by purging with nitrogen. The polymerization is catalyzed at 20° C. with 2 ml of a 0.2% tert-butyl hydroperoxide solution and 3 ml of sulfur dioxide gas, and the batch is heated up to about 100° C. by the generated heat of polymerization.

Before being added to water, the final polymer dispersion is added with 3% 6-nonylphenol ethoxylate with stirring.

The polymer product is comprised of 25 mole-% acrylamide and 75 mole-% of a partially neutralized acrylic acid.

EXAMPLE 3

In this example, the active substance, pyrethrum, which is an extract from Chrysanthemum species, dissolved in hydrocarbons not specified in detail (supplier: Kenya Pyrethrum), is added as early as prior to the actual polymerization. The active substance is largely insoluble in water and is therefore used as part of the oil phase of the water-in-oil polymer dispersion.

The preparation of the monomer solution corresponds to the procedure in accordance with Example 2.

Thereafter, 30 g of Hypermer® 2296 is dissolved in 416 g of Shellsol® D 100 and 100 g of pyrethrum, and the aqueous monomer solution is added with stirring. After formation of the polymer dispersion, it is homogenized with a fast running household mixer, and the polymer dispersion is made free of dissolved oxygen by purging with nitrogen. Catalysis is effected at 20° C. using 2 ml of a 0.2% tert-butyl hydroperoxide solution and 3 ml of sulfur dioxide gas, and the batch is heated up to about 100° C. by the generated heat of polymerization.

Before being added to water, the final polymer dispersion is added with 3% 6-nonylphenol ethoxylate with stirring.

EXAMPLE 4

In this example, the active substance Methoprene® (=isopropyl (E,E)11-methoxy-3,7,11-trimethyl-2,4-dodecane-dienoate) is added as early as prior to the actual polymerization. The active substance is largely insoluble in water and is therefore used as part of the oil phase of the water-in-oil polymer dispersion.

To prepare the polymer dispersion, an aqueous monomer solution is initially produced from the following components:
350 g of water
226 g of acrylamide, 50% solution
344 g of acrylic acid
535 g of potassium hydroxide solution, 45%
0.6 ml of thioglycolic acid
1.0 ml Versenex® 80
5.0 ml of TAMAC
0.3 g of ABAH
0.4 g of VA-044

Thereafter, 30 g of Hypermer 2296 is dissolved in 500 g of Shellsol® D 100 and 100 g of Methoprene®, and the aqueous monomer solution is added with stirring. After formation of the polymer dispersion, it is homogenized with a fast running household mixer, and the polymer dispersion is made free of dissolved oxygen by purging with nitrogen. The polymerization is catalyzed at 20° C. with 2 ml of a 0.2% tertbutyl hydroperoxide solution and 3 ml of sulfur dioxide gas, and the batch is heated up to about 100° C. by the generated heat of polymerization.

Before being added to water, the final polymer dispersion is added with 3% 6-nonylphenol ethoxylate with stirring.

The polymer product is comprised of 25 mole-% acrylamide and 75 mole-% of a partially neutralized acrylic acid (potassium salt).

EXAMPLE 5

In this example, the active substance Methoprene® (=isopropyl (E,E)11-methoxy-3,7,11-trimethyl-2,4-dodecane-dienoate) is added as early as prior to the actual polymerization. The active substance alone forms the oil phase of the water-in-oil polymer dispersion.

To prepare the polymer dispersion, an aqueous monomer solution is initially produced from the following components:
490 g of water
234 g of acrylamide, 50% solution
358 g of acrylic acid
358 g of sodium hydroxide solution, 50%
0.6 ml of thioglycolic acid
1.0 ml of Versenex® 80
5.0 ml of TAMAC
0.3 g of ABAH
0.4 g of VA-044

Thereafter, 30 g of Hypermer® 229.6 is dissolved in 516 g of Methoprene®, and the aqueous monomer solution is added with stirring. After formation of the water-in-oil polymer dispersion, it is homogenized with a fast running household mixer, and the polymer dispersion is made free of dissolved oxygen by purging with nitrogen. The polymerization is catalyzed at 20° C. with 2 ml of a 0.2% tert-butyl hydroperoxide solution and 3 ml of sulfur dioxide gas, and the batch is heated up to about 100° C. by the generated heat of polymerization.

Before being added to water, the final polymer dispersion is added with 3% 6-nonylphenol ethoxylate with stirring.

The polymer product is comprised of 25 mole-% acrylamide and 75 mole-% of a partially neutralized acrylic acid.

EXAMPLE 6

In this example, the active substance, Pyrethrum®, is added as early as prior to the actual polymerization. The active substance is largely insoluble in water and is therefore used as part of the oil phase of the water-in-oil polymer dispersion.

To prepare the polymer dispersion, an aqueous monomer solution is initially produced from the following components:
350 g of water
226 g of acrylamide, 50% solution
344 g of acrylic acid
535 g of potassium hydroxide solution, 45%
0.6 ml of thioglycolic acid
1.0 ml of Versenex® 80
5.0 ml of TAMAC
0.3 g of ABAH
0.4 g of VA-044

30 g of Hypermer 2296 is dissolved in 500 g of Shell-sol® D 100 and 100 g of Pyrethrum®, and the aqueous monomer solution is subsequently added with stirring. After formation of the polymer dispersion, it is homogenized with a fast running household mixer, and the polymer dispersion is made free of dissolved oxygen by purging with nitrogen. Catalysis is effected at 20° C. using 2 ml of a 0.2% tert-butyl hydroperoxide solution and 3 ml of sulfur dioxide gas, and the batch heated up to about 100° C. by the generated heat of polymerization.

Before being added to water, the final polymer dispersion is added with 3% 6-nonylphenol ethoxylate with stirring.

The polymer product is comprised of 25 mole-% of acrylamide and 75 mole-% of a partially neutralized acrylic acid (potassium salt).

EXAMPLE 7

In this example, the active substance, Aquathol® K which is a dipotassium salt of 7-oxabicyclo[2.2.1]-heptane-2,3-dicarboxylic acid, 50% in water, is added as early as prior to the actual polymerization. The active substance is soluble in water and is therefore used as part of the aqueous monomer solution.

To prepare the polymer dispersion, an aqueous monomer solution is initially produced from the following components:
250 g of water
226 g of acrylamide, 50% solution
100 g of Aquathol® K
344 g of acrylic acid
535 g of potassium hydroxide solution, 45%
0.6 ml of thioglycolic acid
1.0 ml of Versenex® 80
5.0 ml of TAMAC
0.3 g of ABAH
0.4 g of VA-044

30 g of Hypermer 2296 is dissolved in 500 g of Shell-sole® D 100, and the aqueous solution is added with stirring. After formation of the polymer dispersion, it is homogenized with a fast running household mixer, and the polymer dispersion is made free of dissolved oxygen by purging with nitrogen. Catalysis is effected at 20° C. using 2 ml of a 0.2% tertbutyl hydroperoxide solution and 3 ml of sulfur dioxide gas, and the batch is heated up to about 100° C. by the generated heat of polymerization.

Before being added to water, the final polymer dispersion is added with 3% 6-nonylphenol ethoxylate with stirring.

The polymer product is comprised of 25 mole-% acrylamide and 75 mole-% of a partially neutralized acrylic acid (potassium salt).

EXAMPLE 8

50 g of a polymer product in accordance with Example 1 (with no active substance added) is mixed with 0.1 g of 3,7-bis(dimethylamino)phenothiazinium chloride. To this end, the polymer product is placed in a beaker, and the active substance is added with continuous stirring.

0.2 g of this formulation is placed on a glass plate having an inclination of 45°. Water (distilled) is applied on the formulation at a rate of 1 ml/min.

As indicated by the blue coloration, the release of active substance continues even after 2 hours.

In a parallel experiment, the active substance itself is placed on the glass plate. The active substance is washed off completely within a period as short as a few minutes.

This Example demonstrates that the formulation significantly reduces the "run off".

EXAMPLE 9

A formulation in accordance with Example 8 is spread on a tire using a brush. Upon admission of water, the blue coloration indicates the release of active substance.

EXAMPLE 10

A water-in-oil polymer dispersion in accordance with Example 1 (with no active substance) is added with varying amounts of Triadimenol® (systemic fungicide). The active substance formulation is applied on wheat (Kanzler) using a conventional seed-dressing unit (Hege company). The ratio of seed and composition according to the invention is 100:1. The wheat thus treated is grown for a short time in a greenhouse. Once the wheat stalks have reached a height of about 10 cm, the stalks are inoculated with *Phytophora infestans*, and the pest infestation is measured after one and 2.5 weeks according to the ABBOTT scale.

In all wheat grains treated with this active substance formulation, a significantly improved development of the test plants can be observed compared to conventionally treated (pickled) wheat grains.

The Table illustrates the efficiency (Abbott) of the samples:

| Example | Triadimenol (ppm/wheat) | W/O Dispersion (%) | Efficiency (Abbott, %, 1 week) | Efficiency. (Abbott, %, 2.5 weeks) |
| --- | --- | --- | --- | --- |
| 10a | 3000 | 1 | 100 | 89 |
| 10b | 2000 | 1 | 100 | 80 |
| 10c | 1000 | 1 | 100 | 77 |
| 10d | 600 | 1 | 92 | 68 |
| 10e | 300 | 1 | 84 | 52 |
| 10f | 100 | 1 | 47 | 36 |
| 10g | 30 | 1 | 23 | 17 |
| 10h | 10 | 1 | 10 | 0 |
| 10i | 3 | 1 | 0 | 0 |
| 10k | 1 | 1 | 0 | 0 |
| 10l | 0 | 1 | 0 | 0 |
| 10m | 300 | 0 | 48 | 39 |

10l, 10m: Control experiments

As demonstrated by the Examples, conventional dressing (10m) has approximately the same effectiveness as active substance dressing using significantly less active substance (10f). In addition, the experiments establish a significant decrease in phytotoxicity when using the composition according to the invention. All the Examples of the invention exhibit improved development of the wheat compared to the sample with conventional dressing.

EXAMPLE 11

A formulation in accordance with Example 9 is mixed with soil (humus-rich soil). The blue coloration after admission of water indicates release of the active substance.

EXAMPLE 12

A formulation in accordance with Example 9 is sprayed on a moist branch using an actuator (commercially available spray device for spraying TLC plates). Upon admission of moisture, the active substance solution undergoes immediate thickening, and the active substance solution remains adhered to the branch.

EXAMPLE 13

Example 11 is repeated, but in this case, a dry branch is used. Together with the composition according to the invention, water is sprayed on the branch. The active substance solution and the water form a gel layer which remains adhered to the branch.

EXAMPLE 14

A few drops of the active substance solution in accordance with Example 4 are placed in a basin (water content about 2.5 l), the drops undergo thickening, forming gel particles from which the Methoprene is gradually released.

What is claimed is:

1. A composition, comprising:
   (A) a water-in-oil polymer dispersion comprising a continuous organic phase virtually immiscible with water, a water-soluble polymer product or a water-swellable polymer product or a combination thereof finely dispersed in said continuous organic phase, and optionally an auxiliary agent; and
   (B) at least one active substance;
   wherein at least one of said water-soluble polymer product or said water-swellable polymer product is obtained in the presence of an ethylenically polyunsaturated monomer as a crosslinker;
   with the provision that no trivalent salt of aluminum is present in amounts capable of crosslinking said water-soluble polymer product.

2. The composition according to claim 1, wherein said active substance is fixed on said water-soluble polymer product or said water-swellable polymer product or both.

3. The composition according to claim 1, wherein said composition consists of:
   a) 20–60 wt.-% of said water-soluble polymer product or said water-swellable polymer product or a mixture thereof, wherein at least one of said water-soluble polymer product or said water-swellable polymer product is obtained in the presence of 0.001 to 10 wt.- % of said crosslinker;
   b) 20–50 wt.-% of said continuous organic phase virtually immiscible with water;
   c) 0.5–10 wt.-% of a water-in-oil emulsifier;
   d) optionally 0.5–10 wt.-% of a-wetting agent;
   e) 0.5–50 wt.-% of said active substance;
   f) water to make 100 wt.-%;
   wherein said continuous organic phase comprises a hydrophobic organic liquid.

4. The composition according to claim 1, wherein said crosslinker is selected from the group consisting of N,N'-methlenebisacrylamide, ethylene glycol diacrylate, ethylene glycol methacrylate, polyethyleneglycol diacrylate, polyethyleneglycol dimethacrylate, propylene glycol diacrylate, butanediol diacrylate, hexanediol diacrylate, hexanediol dimethacrylate, a diacrylate of a block copolymer of alkylene oxide, a dimethacrylate of a block copolymer of alkylene oxide, an addition product of ethylene oxide and/or propylene oxide with glycerol, pentaerythritol di- or triesterified with acrylic acid or methacrylic acid, trimethylolpropane di- or triesterified with acrylic acid or methacrylic acid, a polyhydric alcohol at least diesterified with acrylic acid or methacrylic acid, a polyhydric alcohol at least dietherified with an allyl group, tetraallylethylenediamine, divinylbenzene, diallyl phthalate, polyethyleneglycol divinyl ether, butanediol divinyl ether, divinylethylene urea, triallylamine and a triallylammonium salt.

5. The composition according to claim 1, wherein said water-soluble polymer product or said water-swellable polymer product comprises a monoethylenically unsaturated monomer unit.

6. The composition according to claim 5, wherein said monoethylenically unsaturated monomer is selected from the group consisting of acrylic acid, methacrylic acid, maleic acid, itaconic acid, 2-acrylamido-2-methylpropanesulfonic acid, a salt of acrylic acid, a salt of methacrylic acid, a salt of maleic acid, a salt of itaconic acid, a salt of 2-acrylamido-2-methylpropanesulfonic acid, acrylamide, hydroxyalkyl acrylate and hydroxyalkyl methacrylate.

7. The composition according to claim 1, wherein the active substance is a biologically active substance.

8. The composition according to claim 1, wherein the active substance is a systemic active substance.

9. The composition according to claim 1, wherein the active substance is a non-systemic active substance.

10. The composition according to claim 1, wherein said active substance is selected from the group consisting of a biocide, an inhibitor or a growth promoting substance, a fertilizer, a resistance-enhancing agent, a repellent, an odors substance and a mixture thereof.

11. The composition according to claim 10, wherein said biocide is selected from the group consisting of an acaricide, a bactericide, a fungicide, a herbicide, an insecticide, a larvicide, a molluskicide, a nematicide, a rodenticide, a viricide and a mixture thereof.

12. The composition according to claim 1, wherein said continous organic phase in said water-in-oil dispersion consists entirely or partially of the active substance.

13. The composition according to claim 12, wherein an amount of said active substance in said continuous organic phase is not more than 50 wt. %.

14. The composition according to claim 12, wherein an amount of said active substance in said continuous organic phase is not more than 25 wt. %.

15. The composition according to claim 12, wherein an amount of said active substance in an aqueous phase of said water-in-oil dispersion is not more than 60 wt. %.

16. The composition according to claim 15, wherein an amount of said active substance in said aqueous phase is not more than 40 wt. %.

17. The composition according to claim 15, wherein an amount of said active substance in said aqueous phase is not more than 25 wt. %.

18. The composition according to claim 1, wherein multiple active substances are used.

19. The composition according to claim 1, wherein said composition can be diluted with water to form a viscous solution or dispersion.

20. The composition according to claim 1, wherein said active substance is stabilized.

21. A process for producing the composition according to claim 1, wherein at least one active substance is added prior to, during, or subsequent to the polymerization of the water-in-oil polymer dispersion.

22. The process according to claim 21, wherein multiple active substances are added;

wherein each active substance is added separately to the water-in-oil polymer dispersion or in admixture with other active substances, optionally at various stages of the process.

23. A method of using the composition according to claim 1, comprising:

placing an active substance on or into a substrate or both.

24. The method according to claim 23, wherein said substrate is a plant, a fruit, a field crop or a plant material.

25. The method according to claim 23, wherein said substrate is an insect hotbed.

26. The method according to claim 23, wherein said substrate is a water container, a condensation water container in an air conditioner, a tire, a used tire or combinations thereof.

27. The method according to claim 23, wherein said composition is a spray fluid containing said active substance.

28. The method according to claim 23, wherein said composition is a seed dressing containing said active substance.

29. The method according to claim 23, wherein a run-off effect or a leaching effect is reduced.

30. The method according to claim 23, further comprising the controlled release of said active substance.

* * * * *